United States Patent [19]
Tanguy et al.

[11] Patent Number: 4,856,044
[45] Date of Patent: Aug. 8, 1989

[54] APPARATUS FOR THE DETERMINATION OF THE OSSEOUS MINERAL CONTENT

[75] Inventors: Jean-Claude Tanguy, Athis Mons; Domonique Chambellan, Versailles; Raymond Pommet, Les Essarts Le Roi, all of France

[73] Assignee: Commissaruat A L'Energie Atomique, Paris, France

[21] Appl. No.: 75,048

[22] Filed: Jul. 17, 1987

[30] Foreign Application Priority Data
Jul. 18, 1986 [FR] France ............................... 86 10492

[51] Int. Cl.$^4$ ............................................. H05G 1/02
[52] U.S. Cl. ................................... 378/198; 378/193; 378/197
[58] Field of Search .................... 378/62, 99, 193, 195, 378/196, 197, 198

[56] References Cited

U.S. PATENT DOCUMENTS

| | | | |
|---|---|---|---|
| 4,365,161 | 12/1982 | Dalton et al. | 378/99 |
| 4,635,284 | 1/1987 | Christiansen | 378/197 |
| 4,709,382 | 11/1987 | Sones | 378/62 |
| 4,741,015 | 4/1988 | Charrier | 378/196 |

Primary Examiner—Carolyn E. Fields
Assistant Examiner—David P. Porta
Attorney, Agent, or Firm—Pearne, Gordon, McCoy & Granger

[57] ABSTRACT

Apparatus for determining the osseous mineral content by partial absorption of ionizing rays by a source preferably constituted by two elements. It comprises a mobile carriage on slides and two arms carrying the transmitter block for the radioactive beam and the receiver block and articulated in such a way that the incidence of the beam can either be horizontal or vertical. The receiver block is provided with a plurality of sensors making it possible to produce a bidimensional image.

11 Claims, 6 Drawing Sheets

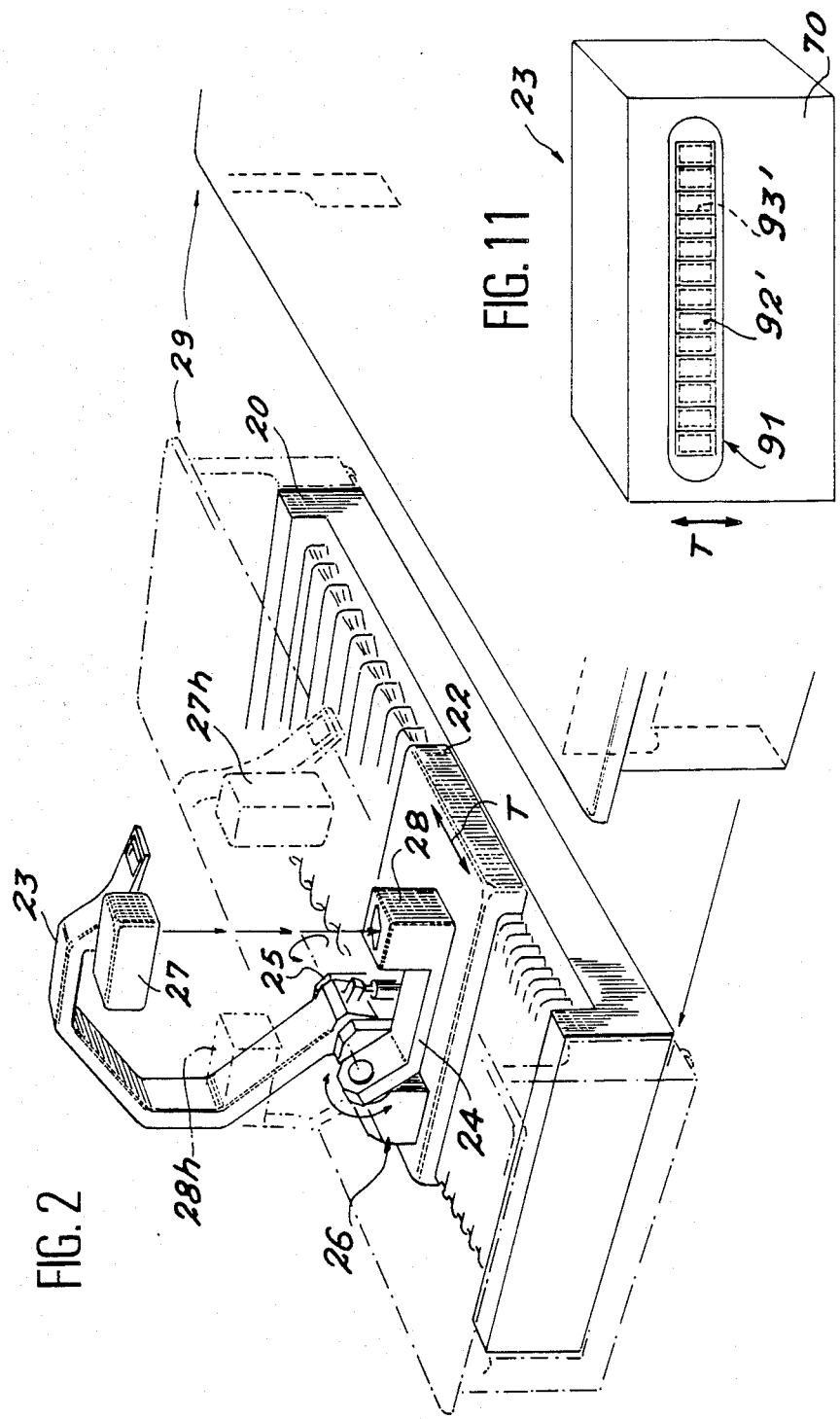

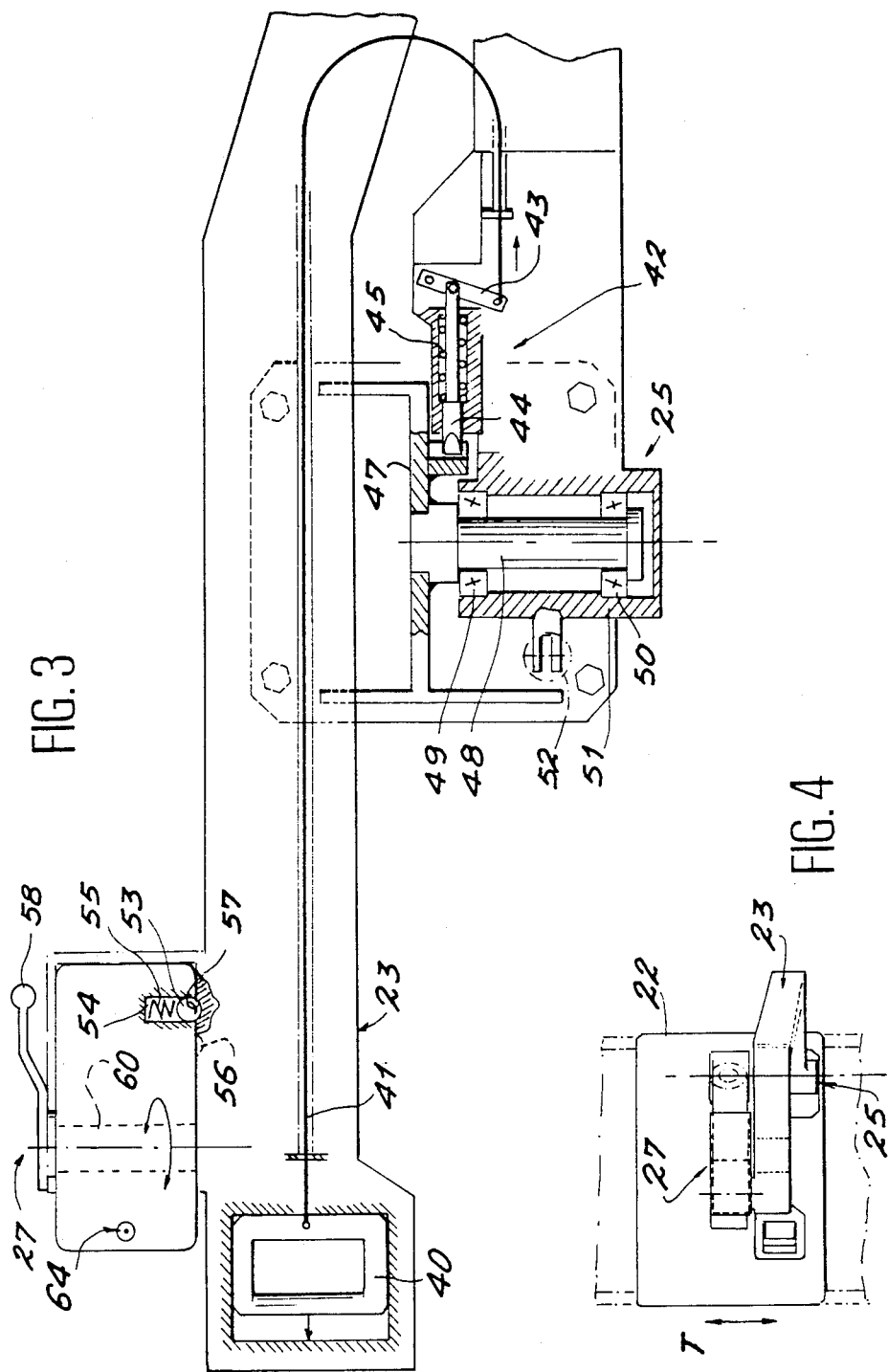

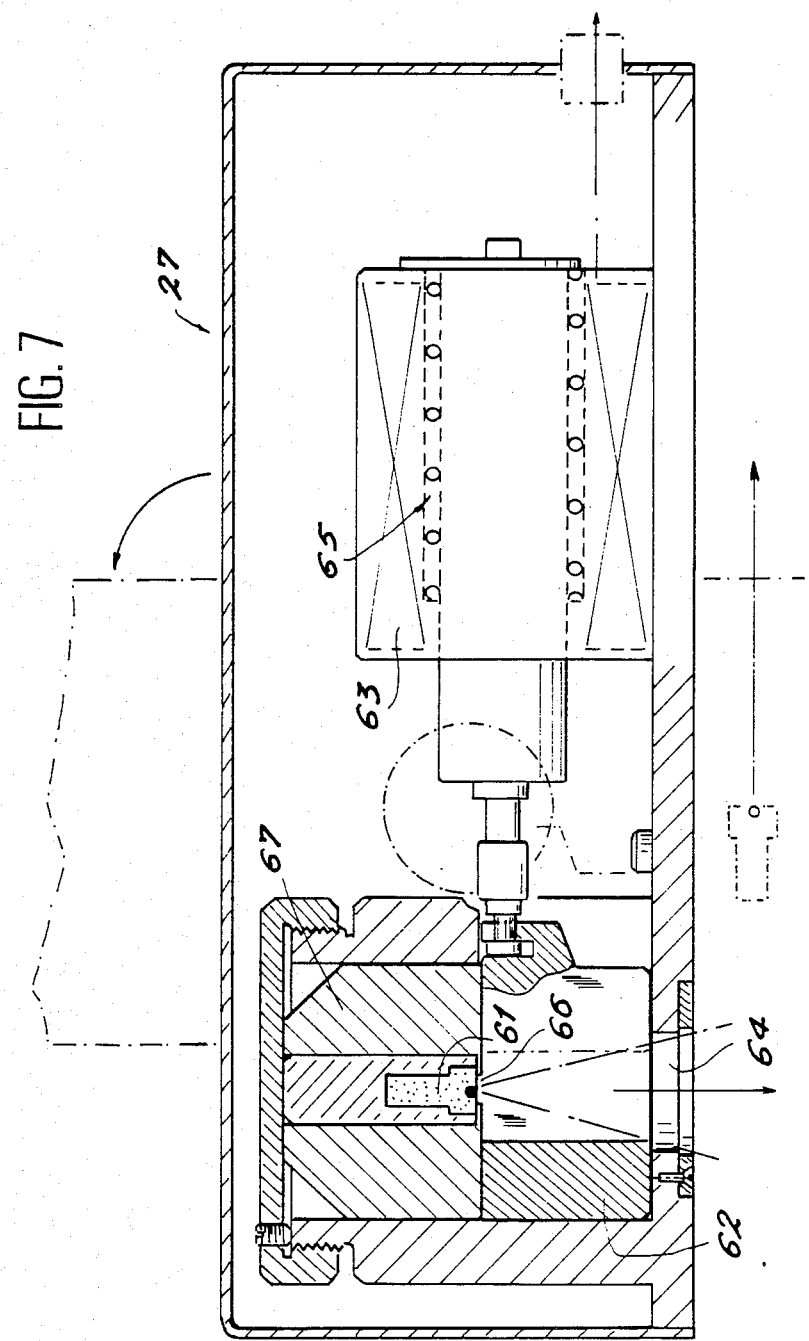

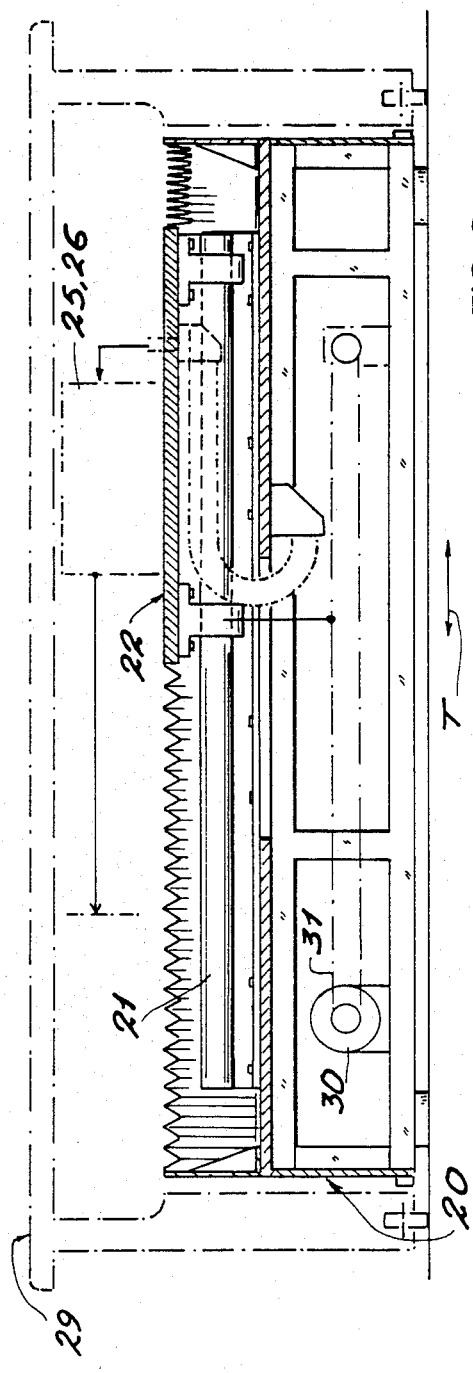
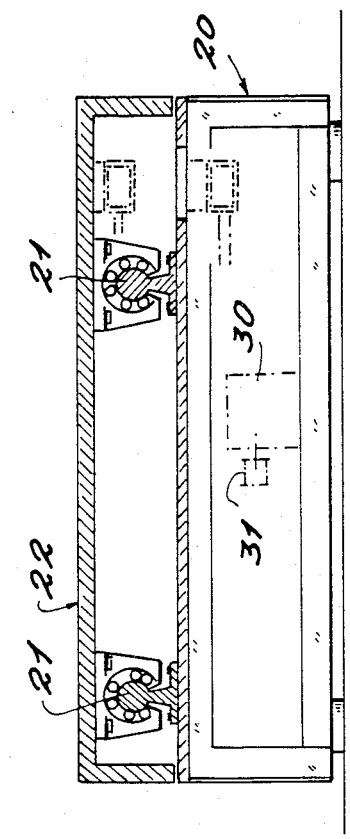

APPARATUS FOR THE DETERMINATION OF THE OSSEOUS MINERAL CONTENT

BACKGROUND OF THE INVENTION

The present invention relates to an apparatus for the detection and visual display of the mineral content of osseous tissues, called an osteodensimeter, as well as, according to a more particular utilization, the application of said apparatus to an efficient and accurate process for measuring the demineralization of the spinal column.

It has long been known that the mineralization of the human skeleton increases in parallel to the growth of the size of the person and can continue for some time following the stopping of this growth until the bones reach a maximum weight at about thirty years of age. After this time, ageing causes the reverse phenomenon, the bones are not completely renewed and their weight progressively decreases. The causes of this process have not been completely explained and are in fact numerous, an important part being played by the genetic constitution of the person and the richness in calcium of his diet. Moreover, this demineralization phenomenon, apart from affecting individual persons in an irregular manner, is selective with regards to the actual bones, so that the spinal column, radius and femur are very sensitive to it, whereas other bones remain intact with age. In principle, women are much more subject to this problem than men. Finally, the demineralization can be linear as a function of time, or may become ever faster. The pathological degree of this process constitutes osteoporosis.

The bone affected becomes increasingly porous and finally loses its mechanical characteristics. It may become unable to fulfill its function and this is manifested by the weakening of the trunk of the person, accompanied by spinal pain, spinal deformation or even the rupture of the column femoris. The latter phenomenon causes a 25% mortality and significant invalidity in other cases. Therefore the costs to the public health service are very high and can only increase as a result of the ageing of the population in developed countries. Prevention can be very advantageous, but this requires detection means adapted to the size of the population at risk (30% of menopausal women suffer from osteoporosis).

Known diagnosis processes involve the irradiation of exposed parts of the body. The method widely used for other applications, i.e. x-rays, is inadequate for a precise diagnosis and only provides a general information in the case of already advanced demineralization. The measurements suffer from the difficulty of faithfully calibrating the radiation source and the exposure and processing characteristics of the film.

Gamma radiation measurement methods have already been developed and they have the double advantage of only slightly radiating the exposed tissues and of being collectable by sensors, such as scintillators, able to translate the partial absorption of the radiation. Gadolinium 153 sources have more particularly been used. This material has the advantage of emitting radiation according to two different energy levels behaving differently with respect to bones and soft tissues, so that it is possible to distinguish the energy absorbed by these tissues from that absorbed as a function of the thickness of the bone, which is all that is of interest for the doctor.

This distinction is made in a satisfactory manner by the use of an analyzer integrated into the measuring cascade and consequently there is no longer any need for using the means necessary with radiation sources having a single energy level, such as immersing the part of the body to be examined in a container of water to simulate a constant thickness of soft tissues, which is valid per se, but not very practical when an entire spinal column is being investigated.

The radiation emitted by gadolinium 153 is relatively sensitive to the fat irregularly contained in the traversed tissues, but on attempting to replace this material it is necessary to use a double source. The authors of the invention have examined this problem before and recommend the use of americium 241 (energy 60 keV, half-life 432 years) and barium 133 (356 keV, 10.6 years) as causing few radiological protection problems and therefore being relatively insensitive to the pressure of fat in the tissues (according to "Mesures de la masse minerale osseuse par attenuation de photons gamma dichromatiques" by D. Tola, R. Hours and J. Boutaine, in "Mesure et signification du volume osseux et de la masse osseuse" by Lavel-Jeantet and Caulin, published by Armour-Montagu in 1982). This improved method gives results with an adequate accuracy, whereas the depth reconstitution of the image of the organism by tomography, which constitutes the best existing investigation process, requires costly equipment, completed by a computer and remains a procedure which is too sophisticated for simple osteoporosis measurements.

Supplementary problems which have given rise to the present invention, however, occur in the case of the very important application of this procedure to the examination of the spinal column. It is therefore necessary to stretch out the patient in a supine position with the legs slightly raised, so as to decrease lordosis. Under these conditions, the most advantageous arrangement consists of placing the radioactive source above the patient and the receiver block below the patient, or vice versa. Thus, the rays emitted are vertical and images from the front are obtained, which have the disadvantage of superimposing the image of the spinal column, which is mainly of interest to the doctor, on that of the posterior arc, which is less subject to demineralization. Thus, the accuracy of the findings is prejudiced by the presence of said posterior arc, particularly as its shape is very irregular.

One might be tempted to position the transmitted block, carrying the radioactive source, and the receiver block on the sides of the patient, so as to obtain a profile image, which would isolate the spinal column, but then the difficulty is encountered of satisfactorily collecting radiation on a continuous band of scintillators due to the dimensions of coupled conventional photomultipliers. Thus, the image is formed point by point with the acid of a single sensor facing the source, so that, apart from prolonged immobilizations, it is necessary to provide a double translation movement of the source and the sensor which can be much more easily accomplished in the case of a vertical beam, because the translations then take place in the horizontal plane and only simple mechanical means are required, which would not be the case if it was necessary to provide a vertical reciprocating movement of a heavy assembly.

SUMMARY OF THE INVENTION

The problem of the present invention is to obviate these various disadvantages. It relates to an apparatus for determining the osseous mineral content by partial absorption of ionizing rays, comprising a block constituted by a radioactive source and another block constituted by a radiation detector positioned facing the source in the working position and separated therefrom by the organic matter to be examined, wherein one of the blocks is connected by an articulation or joint to a first arm, which is itself articulated on a mobile carriage of the apparatus, whilst the other block is integral with a second articulated arm, which is also located on the mobile carriage.

The articulation axis of the first of said arms is parallel to the displacement direction of the carriage, whilst the articulation axis of the second arm is perpendicular to said direction and forms an angle of 45° with the vertical.

It is therefore possible to arrange the apparatus in such a way as to orient the beam horizontally or vertically, whereas a single translation of the carriage is required, because, according to an important feature of the invention, the receiver block comprises a plurality of sensors arranged in one or several rows perpendicular to the displacement direction of the mobile carriage, so that their translation in this direction makes it possible to obtain bidimensional images.

The radioactive source has two energy levels, thus permitting to distinguish absorptions due to bones and soft tissues; the inventors recommend either two elements with a long half-life such as americium 241 and barium 133, or one of the elements such as cesium 137 associated with an x-rays emitter, or the already widely spread gadolinium 153.

The thus designed apparatus is more particularly applicable to a novel process for the determination of the osseous content of the spinal column, wherein it comprises displacing in two scanning directions the mobile carriage along a patient in the supine position on an examination table, the blocks being positioned above and below him for one scan and to his left and right for the other scan, the table being retracted between these two operations to permit the rotation of the two arms. It finally consists of correcting through the use of digital means the time intervals between taking the information concerning the different points located at the same height of the patient by the different sensors of the detector block.

BRIEF DESCRIPTION OF THE DRAWINGS

A possible embodiment of the invention more particularly adapted to the process described hereinbefore is described in non-limitative manner hereinafter relative to the drawings, wherein show:

FIG. 2 is a perspective view of the invention, more particularly showing its kinematics.

FIG. 3 is a plan view of one of the articulated arms according to the invention.

FIG. 4 is the general shape with a slight perspective.

FIG. 7 is a view of the transmitter block with partial section.

FIGS. 8 and 9 are side and front views with partial sections of the device for driving and guiding the carriage.

FIG. 11 is the receiver block and in particular the position of the sensors in another embodiment.

DETAILED DESCRIPTION OF THE INVENTION

Figure 1:
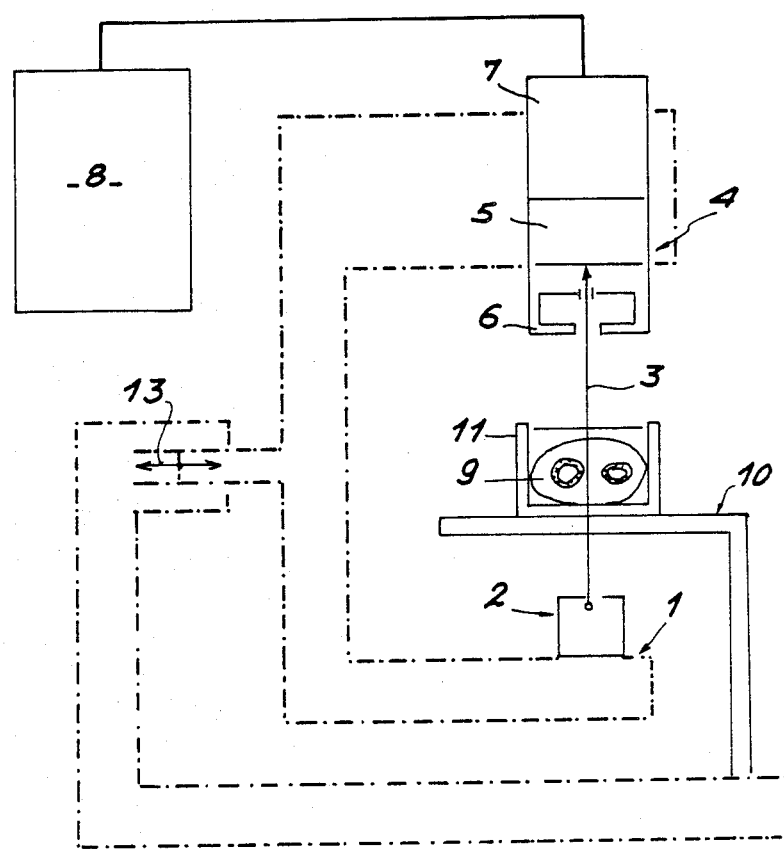
FIG. 1 is a prior art absorptiometry installation diagram.

FIG. 1 illustrates the principle of absorptiometry-based osteodensimeters according to the prior art. On a mobile carriage 1 is placed a radioactive source 2 emitting a parallel beam 3 to a receiver 4 also located on carriage 1 and constituted by a radiation-sensitive scintillator 5 protected by a collimator 6 and completed by a photomultiplier 7, itself connected to a measuring cascade 8, which will be described in greater detail hereinafter, but which essentially comprises a light analyzer and a graphic display means.

On the path of beam 3 is located the organic body to be analyzed, in this case a human forearm 9, which can be seen in section, as well as its radius and cubitus. Forearm 9 rests on the fixed part 10 of the apparatus. In the case of an osteodensimeter with a single radioactive source, it is also necessary to simulate a constant thickness of the soft tissues traversed by the beam. The simplest process consists of immersing the forearm in a water-filled tank 11, which would obviously be much more difficult to carry out in connection with the examination of the spinal column and also less effective due to the heterogeneity of the traversed tissues.

Thus, the measurement consists of displacing carriage 1 with respect to frame 10 in the direction of arrows 13. Thus, there is a distribution of the osseous thickness traversed by the beam 3 over the width of forearm 9, i.e. information translatable by a curve or a line of colored dots as a function of said traversed thickness, in accordance with the principle used for X-ray radiography. Bidimensional images are obtained by juxtaposing such lines by progressive displacement of the carriage 1 in a direction perpendicular to the plane of FIG. 1, which is a slow procedure during which displacements of the body to be analyzed are inevitable.

The realization of the invention shown in FIG. 2 firstly comprises a frame 20 to which are fixed slides 21 shown in FIGS. 8 and 9. They constitute the sliding support of a mobile carriage 22 equipped with two arms 23, 24 articulated at 25, 26 to carriage 22. One of these articulations or joints 25 has an axis collinear to that of slides 21, whilst the other articulation or joint 26 belongs to the plane perpendicular to that referred to hereinbefore and forms an angle of 45° with the vertical. To the end of arm 23 is fixed the transmitter block 27 carrying the ionizing radiation source 61 (FIG. 7) including satisfactorily two radioactive elements having a half-life longer than five years such as americium 241 and barium 133, or x-rays with cesium 137, or gadolinium 153 and equipped with a dense metal protective enclosure, whereas the receiver block 28 containing the radiation sensors is fixed to the end of the other arm 24. However, it would be possible to use the reverse arrangement without prejudicing the spirit of the invention.

Two preferred positions can be defined. In the first, the axis of the emitted beam is vertical and the blocks are in the position defined at 27 and 28 in the drawing. This is the solution adopted by the prior art. In the second preferred position, the axis of the emitted beam is horizontal and the transmitter and receiver blocks are disposed in accordance with 27h and 28h. The rotation operations can take place when the table 29 on which the patient is located has been displaced. The displacement of carriage 22 is brought about in a conventional manner by a motor 30, which drives a belt 31.

Figure 5:
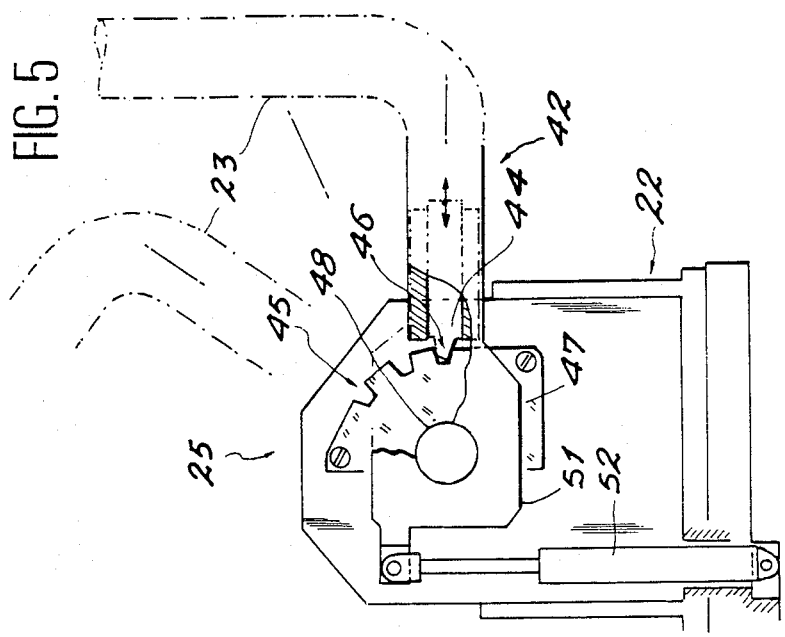
FIG. 5 is the system for maintaining the arm in place.

Arm 23, articulation 25 and transmitter block 27 shown diagrammatically in FIG. 4 will be described in greater detail relative to FIGS. 3, 5 and 7. Arm 23 is provided with a handle 40, whose action releases a bolt 42 by means of a metal cable 41 traversing arm 23. Bolt 42 more particularly comprises a lever 43, which reduces the travel of cable 41 and leads to the retraction of a pawl 44 which can be returned to its initial position by a spring 45, as soon as handle 40 is no longer actuated. Pawl 44 makes it possible to lock arm 23 in the two preferred measurement positions by inserting a fixed bolt 47 in one of the two notches 45, 46. Articulation 25 comprises a shaft 48 connected to the apparatus carriage 22, as well as two ball bearings 49, 50 with oblique contact and which permit the rotation of the bored end 51 of arm 23. The movement of arm 23 is facilitated by a jack 52 connected to said end 51 and ensured by handle 40.

As the preferred measurement directions are perpendicular and the rotation angle imparted to arm 23 is less than 90°, it is necessary to rotate transmitter block 27. A simple system, such as an abutment ball 53 disposed in a recess 54 of block 27, forced by a spring 55 and positionable in two cavities 56, 57 with a complementary shape and located on arm 23, can be used for obtaining the stabilization of the axis of the ionizing beam, the rotation of block 27 being ensured by a sleeve 58 connected thereto and able to move about a shaft 60 connected to arm 23.

The ionizing radiation source 61 is located within a biological protection recess 67 perforated by an opening 66. During the use of the apparatus, source 61 can emit radiation by the displacement of a screen 62 controlled by the excitation of an electromagnet 63. According to the invention, collimator 64 is sufficiently wide to permit the establishment of a divergent and not a rectilinear beam as was the case in FIG. 1. The explanation for this modification will be given hereinafter. A restoring spring 65 makes it possible to blind the ionizing source 61 as soon as the electromagnet 63 is no longer excited.

Figure 6:
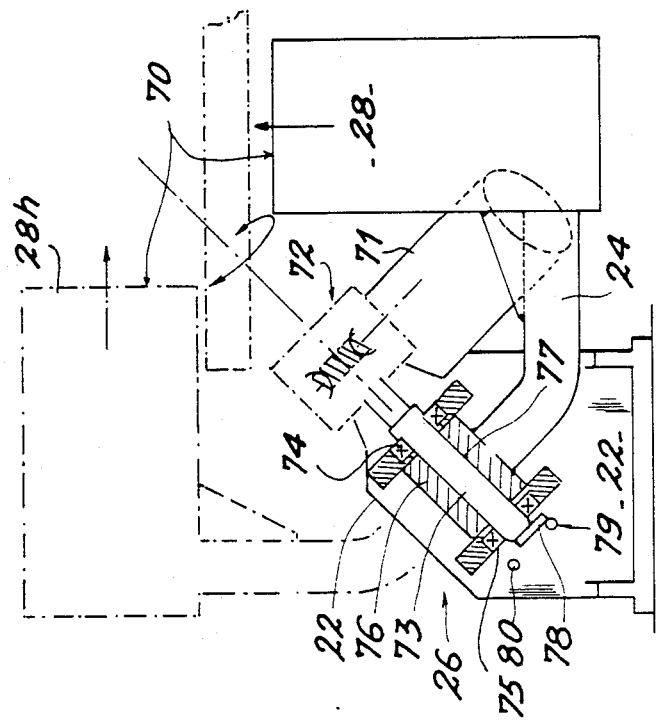
FIG. 6 is the system for maintaining in place and pivoting the other arm.

The mechanism for rotating arm 24 and receiver block 28 is relatively different, as can be gathered from FIG. 6. Arm 24 performs a half-turn to pass from one preferred measuring position to the other, which involved a 90° rotation of the receiver block 28 and its measuring face 70, although it is possible to fix it rigidly on said arm. Rotation takes place with the aid of a motor 71 coupled to a geared motor 72. The rotary movement imparted to shaft 73, supported by carriage 22 by means of two oblique contact ball bearings 74, 75, is taken up by the bored end 76 of arm 24 by means of a negative clearance fit 77. A pin 78 on shaft 73 in turn touches two diametrically opposite contacts 79, 80 making is possible to stop motor 71 and stabilize the receiver block 28 in one or other of the desired positions.

Figure 10:
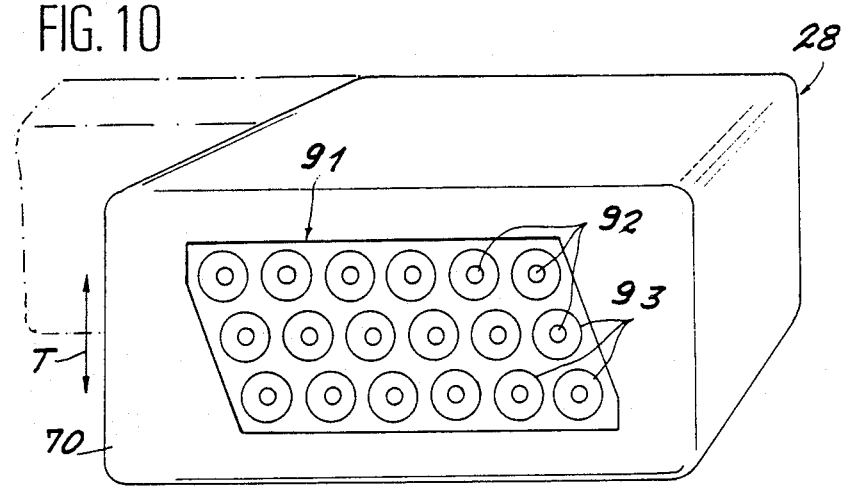
FIG. 10 is the receiver block and in particular the position of the sensors.

On referring to FIG. 10, it can be seen that the face 70 of receiver block 28 has a parallelogram-shaped screen 91 behind which are arranged several rows of scintillators 92 coupled to the same number of photomultipliers 93 positioned behind them and which are much larger. Each pair defines a radiation sensor. Sensitive produces of scintillators 92 can be chosen among NaI, CsI, BiGeO, CsF, CaFr, CdTe and $HgI_2$ particularly.

As the carriage 22 performs a single translation in accordance with the double arrow T and the patient remains stationary on table 29, a bidimensional image can only be obtained by scanning a group of sensors, each of which simultaneously records the information supplied by part of the beam emitted by the ionizing source 61. The most obvious idea would be to position the sensors in accordance with a line on face 70 and perpendicular to direction T. However, this cannot be readily used as a result of the dimensions of the conventional photomultipliers 93 or the equivalent devices used in place thereof, such as photodiodes or semiconductors, because the resolution of the images would be inadequate.

Thus, in order to solve this problem, use is made of sensors arranged in several rows, three rows in FIG. 10, each row comprising six sensors. The inventors consider that other configurations would also give good results. This arrangement obviously requires an adapted shape of the collimator 64. It also implies that simultaneously collected information does not relate to points located at the same height of the patient. Account must be taken of this in the flow chart for producing the image, e.g. by means of a timer located in the measuring cascade, the gap between two rows perpendicular to direction T being equivalent to one time interval as a result of the translation of carriage 22. It is obviously also necessary to prevent, by preliminary calibration, possible disparities in the intensity of the radiation on each sensor. Other sensor distributions, such as in staggered manner, can be used without passing beyond the scope of the invention.

It must however be mentioned that photomultipliers 93' with multiple photocathodes, which have recently appeared, have a much reduced size and thus allow to join neighboring scintillators 92', as shown in FIG. 11. The scintillators 92' now have a rectangular shape and constitute a continuous row; photomultipliers 93' are hidden behind them. Only one row, constituted of twenty-four sensors for example, is required in this embodiment. The process of creating an image with adequate solution is of course greatly simplified.

Thus, the invention provides an interesting solution to the problems presently caused in connection with the precise measurement of osseous dimineralization, mainly in the vertebrae, which are among the most affected bones. In this precise case, it might firstly be desired to take an image of the spinal column in vertical incidence, as is usually the case. The transmitter block 27 and receiver block 28 are arranged as in FIG. 2 and the measurement is carried out by moving carriage 22. After moving away table 29, the receiver block assumes the position indicated at 28h. The table 29 is then returned into place and the transmitter block is moved to the position 27h. It is then possible to make a profile image of the spinal column, so as to be able to distinguish the image of the spinal column, which is the only part affected by osteoporosis, from that of the posterior arc. It is advantageous to match table 29 and frame 20, so as to position them with a slight clearance, as shown in FIG. 8. During the examination, the table is immobilized by not shown locking jacks.

The choice of a group of sensors makes it possible to use a single translation mechanism for the carriage 22. The simultaneity of the measurements involves a significantly reduced examination time when using the prior art radioactive sources. However, it is advantageously possible to use lower fluence radioactive sources (number of gamma photons emitted per unit of surface and time). The acquisition time of the measurements at each point must be extended, which limits the examination time gains which could be expected. However, it is possible to use much less costly and durable sources than gadolinium 153, in particular americium 241 and barium 133, which have a much longer half-life. It is possible to use a combination employing an appropriately filtered x-radiation produced by an x-ray tube and a radioactive source. X-radiation can replace the low energy element, e.g. americium 241.

The simplicity of a mechanism making it possible to effect examinations in accordance with two perpendicular incidences, but which requires the use of a number of sensors, the advantage of which is that a more interesting radioactive source can be used, justifies the interest of the present invention.

What is claimed is:

1. Apparatus for the determination of the osseous mineral content of a patient by partial absorption of ionizing rays, comprising a block constituted by a source of ionizing rays and another block constituted by a radiation detector, the source and the detector facing one another during observations of a patient and the patient being then between the source and the detector, wherein one of the blocks is articulated on a first arm about an axis directed in a first direction, the first arm being articulated on a support about an axis directed in the first direction, the other block being secured to a second arm articulated on the support about another axis perpendicular to the first direction.

2. Apparatus for the determination of the osseous mineral content according to claim 1, wherein the support is a carriage moveable in the first direction.

3. Apparatus for the determination of the osseous mineral content according to claim 1, wherein the first direction is horizontal and the axis of the second arm articulation is directed with an angle of 45° from vertical direction.

4. Apparatus for the determination of the osseous mineral content according to claim 1, comprising means for locking the two arms on the support and the articulated block on the first arm.

5. Apparatus for the determination of the osseous mineral content according to claim 2, wherein the detector is made of a row of photomultipliers, the row being perpendicular to the first direction.

6. Apparatus for the determination of the osseous mineral content according to claim 2, wherein the detector is made of several parallel rows of sensors, the rows being perpendicular to the first direction, orthogonal projections of the sensors on a plane perpendicular to the first direction defining equal gaps smaller than the dimensions of the sensors.

7. An apparatus for determining the osseous mineral content according to claim 5, wherein the photomultipliers of the detector block are arranged in several rows perpendicular to the first direction of the mobile carriage and wherein their arrangements in accordance with an orthogonal projection on a plane perpendicular to said direction defines equal gaps between two photomultipliers, the gaps being smaller than the diameters of the photomultipliers.

8. An apparatus for determining the osseous mineral content according to claim 5, wherein the ionizing ray source is constituted by one or more radioactive elements having a half-life exceeding five years.

9. An apparatus for determining the osseous mineral content according to claim 7, wherein the ionizing ray source is constituted by a radioactive element having a half-life exceeding five years and an x-ray source.

10. An apparatus for determining the osseous mineral content according to claim 5, wherein the ionizing ray source includes americium 241 and barium 133.

11. Process for the determination of the osseous mineral content of the spinal column of a patient lying on a table in supine position, comprising the steps of:

displacing for a first observation, in a horizontal longitudinal direction along the table, a mobile carriage provided with two arms, one of the arms being articulated on the carriage about an axis oriented in the horizontal longitudinal direction and the other arm being articulated on the carriage about another axis perpendicular to the horizontal longitudinal direction and at an angle of 45% from the vertical direction, a first block being articulated on the first arm about the horizontal longitudinal direction and a second block being secured to the second arm, one of these blocks carrying a source of ionizing rays and the other block carrying a detector comprising at least one row of sensors, the at least one row being perpendicular to the horizontal longitudinal direction, one of the blocks being above the table and the other block being beneath the table;

rotating the second arm 180° around the carriage, the first arm a first angle inferior to 90° around the carriage and the first block a second angle inferior to 90° about the first arm, the sum of the two angles inferior to 90° being substantially equal to 90°; and again displacing the carriage for a second observation in the horizontal longitudinal direction along the table, the blocks being then at the right and the left of the table.

* * * * *

UNITED STATES PATENT AND TRADEMARK OFFICE
CERTIFICATE OF CORRECTION

PATENT NO. : 4,856,044
DATED : August 8, 1989
INVENTOR(S) : Jean-Claude Tanguy, Domonique Chambellan, Raymond Pommet It is certified that error appears in the above-identified patent and that said Letters Patent is hereby corrected as shown below:

Column 2, line 18, delete "pressure" and insert --presence--.

Column 2, line 48, delete "transmitted" and insert --transmitter--.

Column 2, line 55, delete "acid" and insert --aid--.

Column 6, line 42, delete "solution" and insert --resolution--.

Column 8, line 33, delete "45%" and insert --45°--.

Signed and Sealed this

Twenty-sixth Day of June, 1990

Attest:

HARRY F. MANBECK, JR.

*Attesting Officer*  *Commissioner of Patents and Trademarks*